United States Patent [19]

Clark

[11] Patent Number: 4,976,622

[45] Date of Patent: Dec. 11, 1990

[54] DIABETIC DIET PLAN AID AND METHOD

[76] Inventor: Rita M. Clark, 2317 Valleybrook Dr., Toledo, Ohio 43615

[21] Appl. No.: 422,591

[22] Filed: Oct. 17, 1989

[51] Int. Cl.$^5$ ............................................. G09B 19/00
[52] U.S. Cl. ..................................... 434/127; 434/238
[58] Field of Search .............. 434/127, 430, 128, 129, 434/238

[56] References Cited

U.S. PATENT DOCUMENTS

| | | | |
|---|---|---|---|
| 2,337,594 | 12/1943 | Easley | 434/127 |
| 2,883,765 | 4/1959 | Blaine | 434/238 |
| 3,290,796 | 12/1966 | Gurda | 434/238 |
| 3,491,715 | 1/1970 | Longarini | 434/127 X |
| 3,841,260 | 10/1974 | Sharp et al. | 434/127 X |
| 4,310,316 | 1/1982 | Thomann | 434/127 |
| 4,606,555 | 8/1986 | Adams | 434/127 X |
| 4,652,241 | 3/1987 | McCarty | 434/127 |
| 4,832,603 | 5/1989 | Basi | 434/127 |
| 4,863,386 | 9/1989 | Makey | 434/238 X |

OTHER PUBLICATIONS

*Behavior Res. and Therapy;* 1975, vol. 33; pp. 333–337, "Case Histories and Shorter Communications".

*Primary Examiner*—Richard J. Apley
*Assistant Examiner*—Rachel M. Heaky
*Attorney, Agent, or Firm*—Charles F. Schroeder

[57] ABSTRACT

A system to aid a person in learning a prescribed diet, including food groups, allowed food portions, prescribed meal and medication schedule in which a two panel folder is provided, each panel having a set of pockets labeled for each meal and snack of a day of the diet. A clock face is pictured on each pocket, showing the average meal time, such as for a patient with diabetes and a space on each pocket for the patient to pencil in his own time for meals, if it differs from the pictured time. Several tickets or cards are also provided labeled with food group choices and medication, optionally with a picture symbol representative of the particular food group or medication. On the back of each card is a list of several foods and allowed portions of the prescribed diet, each card list being different to help the patient plan meals with different allowed foods.

According to the method of the invention the patient first matches cards listing the items and portions of food allowed for each meal or snack, then places the food cards into the pockets of one panel of the folder representative of the meals and snacks of one day of the diet. If medication is prescribed, matching tickets are placed in the meal pockets that meet the medication schedule. Starting with breakfast, as the patient takes medication or uses each food portion allowed at the prescribed time, he takes the matching card from its respective pocket, and places it into the corresponding pocket on the other panel of the folder. This procedure is repeated for each meal or snack item consumed during the given day whereby at the end of the day all cards of items consumed will be transferred to the pockets of the other panel of the folder, ready for the next day's use. No need exists to reset the cards unless the prescribed diet is changed.

14 Claims, 2 Drawing Sheets

| 20a$_1$ | 20b$_1$ | 20c$_1$ | 20d$_1$ | 20e$_1$ |
|---|---|---|---|---|
| MEAT<br>CHICKEN 1OZ<br>TURKEY 1OZ<br>ALL FRESH AND FROZEN FISH 1OZ<br>OYSTERS MED 6 | VEGETABLE<br>BRUSSEL SPROUTS ½C<br>CABBAGE, COOKED ½C<br>CARROTS ½C<br>BEETS ½C<br>OKRA ½C | BREAD (STARCH)<br>BRANFLAKES ½C<br>READY TO EAT CEREAL NON SWEETENED ¾C | FRUIT<br>[illegible] | FAT<br>[illegible] |

| 20a$_2$ | 20b$_2$ | 20c$_2$ | 20d$_2$ | 20e$_2$ |
|---|---|---|---|---|
| MEAT<br>EGG 1<br>EGG WHITES 3 WHITES<br>PEANUT BUTTER 1 TBSP | VEGETABLE<br>PEPPERS GREEN ½C<br>PEA PODS ½C<br>SAUERKRAUT ½C<br>ARTICHOKE ½ MED SIZE | BREAD<br>[illegible] | FRUIT<br>JUICES<br>ORANGE ½C<br>GRAPE ⅓C<br>APPLE ½C<br>PINEAPPLE ½C<br>PRUNE ⅓C | FAT<br>[illegible] |

| 20a$_3$ | 20b$_3$ | 20c$_3$ | 20d$_3$ | 20e$_3$ |
|---|---|---|---|---|
| MEAT<br>CHEESE<br>ANY COTTAGE CHEESE ¼ CUP<br>MOZZARELLA 1OZ<br>DIET CHEESES 1OZ | VEGETABLE<br>[illegible] | BREAD<br>[illegible] | FRUIT<br>[illegible] | FAT<br>[illegible] |

FIG. 3

DIABETIC DIET PLAN AID AND METHOD

BACKGROUND OF THE INVENTION

The present invention is a device and method to aid in learning and maintenance of a prescribed or planned diet and more specifically to a portable means and planning aid by which a clear record and indication is provided to a user and others of what has been consumed by the user at any particular time of day in compliance with the diet and simultaneously with the diet being followed the diet plan for the next day is virtually self prepared.

The invention has particular value as an aid to persons required to follow a physician's prescribed diet such as diabetic patients but also has meaning and value in use by persons following balanced diets and exercise regimens recommended for weight control such as the WEIGHT WATCHERS weight loss diet.

A major problem facing a person who is to follow a newly prescribed diet is the usual necessity to break existing eating habits and to discipline himself or herself daily to both learn and follow the new diet. In this process the dieter must learn not to duplicate nor forget what items of the diet have been and are to be eaten during any given meal until the eating patterns of the new diet become second nature. In this regard the person following a diet usually records what has been eaten as it is consumed during the day but frequently recording items consumed is overlooked, and the question arises as to what was or is to be consumed.

The invention is described and exemplified herein by a diet plan aid comprising exchange units for persons afflicted with diabetes. Persons with diabetes have a problem with glucose, a form of sugar made by our body from the food we eat. It is used to produce energy. For the body to use glucose properly, however, it needs insulin which regulates the amount of glucose the body makes use of.

Treatment of diabetes aims to keep blood sugar as nearly normal as possible. This requires maintaining a balance between diet, insulin and exercise. For many people with diabetes, proper diet is all that is necessary for treatment. The diabetic diet is a well balanced diet that is planned for each individual's needs. The doctor prescribes the type of diet and the dietician helps the person fit the diet into his or her daily life. In addition to assisting in development of patterns or habits of medication and food consumption the invention is also adaptable to inclusion of prescribed exercises that are to be followed during specific times of the day.

An object of the invention is to make it an easy task for persons to learn a newly prescribed diet by providing a running record of items consumed as well as an indication of items yet to be consumed at each time of the day.

Another object of the invention is to provide a running visual indication for the user as well as those monitoring the user's progress whether the diet is being followed as prescribed.

The invention is a method and means whereby a prescribed diet can be assembled from a series of food cards or tickets, each listing a food group or classification of food of a diet, including medication to be consumed at specified times during the day as at breakfast, lunch, dinner and interspersed snack times. As a means for carrying out the method, a booklet or folder is provided having two or more pages in the form of panels on opposite sides of a fold, each panel being representative of and displaying a day of meals and snacks of the user's diet. The folder herein more specifically described has two panels joined in hinged relation at adjacent edges representing two days of the user's diet. The panel for each day is provided with a series of horizontal card holding pockets aligned in one or more vertical rows wherein each pocket is representative of a meal or snack corresponding to a time of day for consumption of an item of food of the diet. More specifically, the pockets are provided to represent times for breakfast, lunch and dinner as well as times for snacks and times for taking medication. Food cards listing the items matched to each of the meals and snacks of the diet are assembled and inserted in the pockets representing the meal time or snack time during which the specific items of food of the diet are to be consumed.

The food cards each lists a specific food group or classification of food such as meat, vegetable, fruit, fat, bread and milk termed exchanges. Each food classification or exchange card also lists a number of specific items of food falling within the classification as well as the size of portion of each such item allowed in the diet. Such specific food listings may be on the obverse side of the face on which the broad food group is identified. The cards thereby provide specific diet food items which meet each day's prescribed diet or food and permit the diet to be assembled and represented by selection of appropriate cards from the total number of cards. Thus the user is provided a listing of options within each classification of food prescribed permitting a range of variety within the prescribed diet.

The diet cards are assembled into subsets according to the breakfast, lunch and dinner parts of the diet as well as the snack time part. Each subset is placed in one of a series of pockets each representing the meal or snack to be consumed according to the diet. As each item of food of the meal or snack of the diet plan for a given day is consumed, a card listing such item is removed from its representative meal time pocket and is placed in a corresponding meal time pocket of the panel representative of the following day. The diet program for the next day is thus progressively prepared as the current day's diet is consumed.

In other words, in using the diet aid of the invention, cards for the full day of a user's diet are first inserted in appropriate mealtime pockets of the current day panel such as the panel on the left in a booklet. As the day progresses and as each prescribed item has been consumed by the user, the card corresponding to the item consumed is transferred from the pocket of the meal being consumed to the pocket of the corresponding meal in the next panel corresponding to the following day. This procedure is followed successively for each meal. At the end of the day, if the diet is followed properly, all cards for the given day will have been removed and transferred to appropriate pockets for the next day. Thus at any time of day or at the end of the day the patient, nurse or doctor can observe from the cards remaining in the pockets which of the items were or were not consumed by the patient during the day. Meanwhile, the consumed items will have already been transferred to the next day's pockets for programming of the next day's meals.

It is therefore apparent that beside offering a program for guiding the user's eating activities, the booklet and associated cards provide an instant report to the patient as well as others looking at the booklet as to whether the diet has been followed and what deviations might have occurred so that corrective action might be taken to balance the diet in the following day's eating program.

Although food and medications have been referred to in describing the program of the invention it will be readily recognized that prescribed exercises to be conducted during specified times during the day can also be represented by cards inserted in appropriate time pockets.

A feature of the invention is that as the diet for any one day is followed the program for the next day is prepared automatically.

Another feature of the invention is the ease with which a diet can be programmed into the device and the ease with which by use of the invention new diet habits can be established.

Still another feature of the invention is that it is particularly helpful in instructing and guiding youngsters in establishing new diet habits where unfamiliarities with the whys and wherefores of following a diet has in the past presented difficulties to learning new habits.

Other objects and features which are believed to be characteristic of my invention are set forth with particularity in the appended claims. My invention, however, both in organization and manner of assembly, together with further objects and features thereof may be best understood with reference to the following description taken in connection with the accompanying drawings.

FIG. 3 is an illustration of different food group cards provided in the diet kit and examples of different listings of optional items which may be set out on different cards of the same food group.

Figure 1:
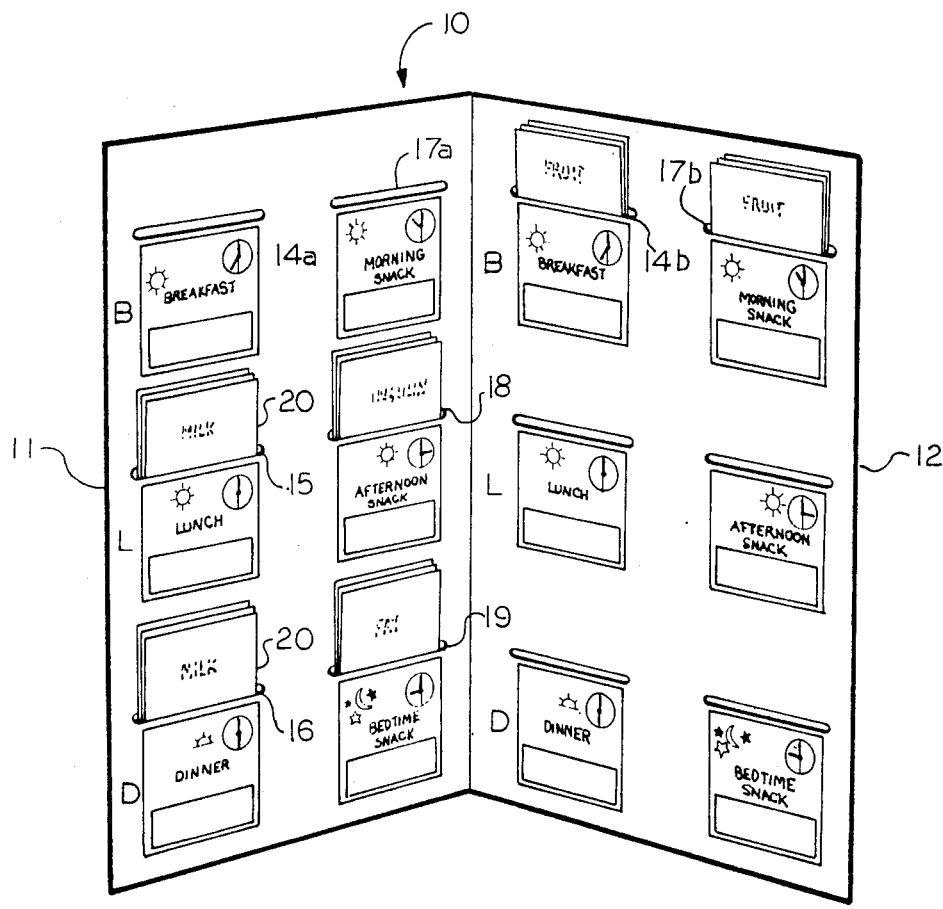
FIG. 1 is a view of a diet kit folder with pockets representing meals and snacks of a daily diet on two days, the current and succeeding day, with cards inserted in the pockets representing food groups to be consumed during the represented meals and snacks.
Figure 2:
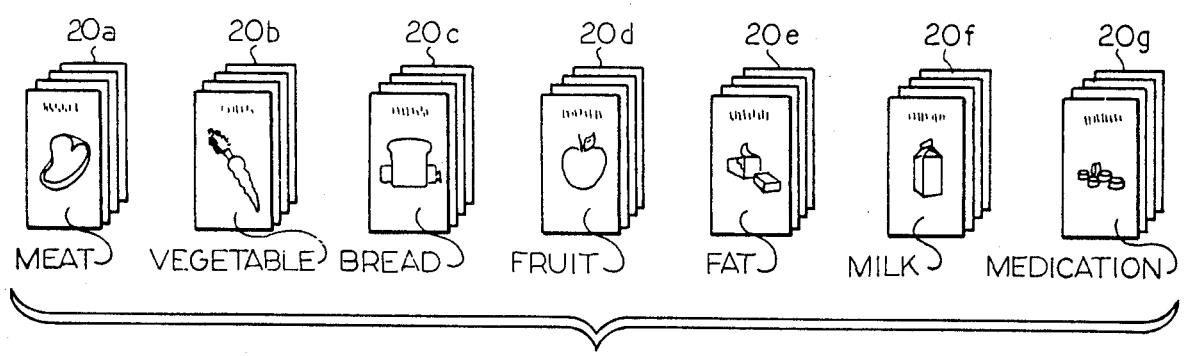
FIG. 2 illustrates cards of different classes of food groups which can be assembled into meal and snack subsets listing the food items which may be consumed in each representative meal of the diet.

Referring to the drawing in greater detail, the folder and food cards can be provided in the form of a kit as illustrated in FIGS. 1 and 2. The folder 10 which can be made of stiff cardboard material has two panels 11 and 12 representative of two days of a user's prescribed diet. The kit as herein described is particularly designed for persons such as diabetic patients who are required to take prescribed medications and are to consume a balanced diet of specified food groups at prescribed times during the day. The kit includes the folder with cards 20 each of which represents a food group identified by a generic term such as meat, bread, fruit, etc. on its face. A printed listing of optional specific items of food which fall within the generic food group identified on the face of each card is provided on the obverse side of the card The portion or quantity of each item which is allowed in the diet is also indicated adjacent each of the listed items.

The folder has a series of pockets for holding the diet cards, each pocket being representative of a time of day and a meal or a snack. The cards 20 are first assembled into sets or sub-groups including the foods for consumption during the specified periods of the day. The card sets are placed in a correspondingly identified pocket of a current day panel of the folder. Breakfast, lunch and dinner pockets as well as snack time pockets are aligned in vertical rows on the face of each of the daily panels 11 and 12. The assembled card sets representative of each food consumption period and listing the diet items to be consumed are first placed in the pockets for one day of the folder. As the items of the diet are progressively consumed, the user removes a corresponding card from its pocket for each of the items consumed and places it in the corresponding pocket of the adjacent panel representing the following day.

By way of example and as shown in FIG. 1, the cards listing the items which were consumed were transferred from the breakfast pocket 14a of the first day panel 11 to the breakfast pocket 14b of the succeeding day's panel 12 thus indicating that all breakfast items had been consumed on the first day. Similarly, cards representing the consumed morning snack items were removed from snack pocket 17a and transferred to snack pocket 17b of panel 12 for the next day of the folder. Thus, when the folder is viewed by the patient, or someone other than the patient, such as the doctor or nurse, it will be clearly visible to such person that the diet had been followed through the time of the morning snack and that the lunch portion of the diet is yet to be consumed. By repeating the card transfer for each item of each meal and snack during the day, the cards will all have been transferred at the end of the day thereby having programmed the diet for the next day. No resetting of the cards thus is necessary for the next day unless the diet is to be changed.

That is, the cards are thus made ready for use on the next day when they are individually removed and transferred back to the appropriate pockets of the first panel each time an item of the diet is consumed. In addition to labeling each pocket such as for breakfast, morning snack, lunch, afternoon snack, etc. the pocket can also be provided a time indication such as a clock face showing the time when the meal or snack is to be consumed. More specifically, it can be seen from the clock symbols 24, 25 and 26 in FIG. 1 that breakfast is to be taken at 7 a.m., lunch at noon and dinner at 6 p.m. respectively. In the same manner, the clock faces 27, 28 and 29 indicate that the morning snack is to be taken at 10 AM, the afternoon snack at 3 PM and the bed time snack at 9 PM, respectively. A block space 30 is also provided adjacent each clock face time indicator for pencilling in a more precise time should the prescribed times deviate from the average time indicated for food consumption.

FIG. 2 illustrates that a number of cards are provided for each food group, namely, meat group cards 20a, vegetable group cards 20b, bread group cards 20c, fruit group cards 20d, fat group cards 20e milk group cards 20f and diabetic medication cards 20g. The generic group cards can be made more distinguishable from each other by providing a pictorial illustration on all cards of a group represented, such as a slice of bread for the bread group or a meat chop for the meat group. In addition, a different color can be provided for each group, if desired. The total list of items acceptable in each generic group is divided into a partial list on each card. The total number of cards list virtually all items prescribed in diabetic diets. For example, the meat group cards each contain a different partial list of items of the meat group such that with about 11 meat cards, practically all items which might be prescribed in a diet will be included. Similarly, the vegetable group is represented by the partial listings on approximately 5 cards, the bread group by 13 cards, the fruit group by 5 cards, the fat group by 6 cards, and the milk group by 5 cards. Diabetic medication represented by 6 cards are provided in adequate number to correspond to the number of times medication is to be taken during a single day.

FIG. 3 illustrates by way of example the manner in which the back side of each of the cards of each group is provided a different listing of items from other cards of the same group and the allowable portions of each of the items of the group represented by the card. Three cards of the meat group are illustrated exemplifying the types of items included on the different listings on each card. The first illustrated card 20a of the meat group cards lists Chicken - 1 oz. Turkey - 1 oz. or Fresh or Frozen Fish - 1 oz., Oysters, medium - 6. Another meat group card, $20a_2$ lists Egg - 1, Egg Whites - 3 whites and Peanut Butter - 1 tbsp. The next meat card $20a_3$ lists Cheese, any Cottage Cheese - ¼ cup, Mozzarella - 1 oz. and Diet Cheese - 1 oz.

Further, the vegetable group cards 20b exemplified by two cards $20b_1$ and $20b_2$, of the 11 vegetable cards lists in the first card Brussel Sprouts - ½ c., Cabbage, cooked - ½ c., Carrots - ½ c., Beets - ½ c. and Okra - ½ c. The second vegetable card lists Peppers, green - ½ c., Pea Pods - ½ c., Sauerkraut - ½ c., and Artichoke - ½ med. size. The bread group represented by card $20c_1$ lists Bran Flakes - ½ c., and Ready to Eat Cereal non/sweetened - ¾ c. The fruit cards 20d represented by fruit card $20d_2$ lists Juices, Orange ½ c., Grape - ⅓ c., Apple - ½ c., Pineapple - ½ c., and Prune - ½ c. The diabetic medication cards 20g lists on the back side in each case insulin. In this instance, the patient would usually be informed individually of the prescribed times for taking medication and the quantity to be taken. It will thus be seen that each of the cards of the total number is different from the others and is adaptable to being assembled into meal and medication sets corresponding to any of virtually all diets which might be prescribed for a diabetic patient.

If insulin or oral diabetic medication is prescribed, an insulin or diabetic medication card is placed in front of the cards in the pocket that matches the time when the medication is to be taken. If the meal and snack times printed in the clock faces of the booklet do not match the schedule prescribed for the patient, the prescribed times can be marked with a pencil in a space 30 provided on the pocket. If insulin or diabetic medication is taken before breakfast the breakfast dose is first taken and then the corresponding card is removed from the pocket and transferred to the corresponding pocket of the panel for the next day.

It will be recognized that the method and device of the invention lends itself to incorporation of a series of more than two panels which might be extended to a period such as a week. In addition, the invention lends itself to acceptance of a range of cards representative of foods, medication, exercises or inclusion of other specific items of a regimen such as relaxation periods to be followed daily. Further, the regimen programmed by the invention might also be shorter than a one day plan. For example, the plan might be based upon hourly repetition.

The means for holding the cards of the invention might also be in another form such as means utilizing adhesive or Velcro overlays instead of pockets for holding the cards. The daily panels might also be stacked rather than hinged in a folder. The folder also can be of shirt or coat pocket size for convenience in use.

In view of the foregoing, while the invention has been described with regard to an illustrated embodiment, it will be recognized that it is not limited specifically to the particular arrangement shown and described, and accordingly, by the appended claims all modifications, adaptations and arrangements thereof are contemplated which fall within the spirit and scope of the invention.

I claim:

1. A diet plan aid comprising a kit including panels representative of successive days of a diet plan,
    said panels each having pockets therein representative of and identifying food consumption times of the diet comprising breakfast, lunch, dinner and snack times,
    said pockets being positioned on each of said panels in sequence according to the times of day at which specified foods of the diet are to be consumed,
    said kit also including a series of cards each identifying food group choices of the diet to be consumed,
    said cards being sorted into subgroups each including the specific items of food of the diet plan to be consumed at a specified time during the day of said diet plan said subgroups being matched to said corresponding food consumption times of the diet,
    said subgroups each being removably placed in a pocket of one of said panels representing the time of day during which the specific items of the subgroup cards of the day represented by said one panel are to be consumed,
    said subgroup cards each being arranged to be withdrawn from its respective panel pocket and transferred to the corresponding pocket of the panel representative of the following day when the item of food which it represents is consumed whereby an indication is provided on said one panel as to which of the diet items have been consumed while preparing the diet program for the following day of the plan.

2. A diet plan aid as set forth in claim 1 in which said cards which lists choices including a number of specific items including at least one which complies with the requirement of th planned diet whereby foods to be consumed during specified times of a day of the diet can be assembled in a set of cards including all of the specific items to be consumed at such times of the day.

3. A diet plan aid comprising a pair of panels representing two days of a daily diet
    an identical arrangement of card-holding pockets on each of said panels,
    each said arrangement of pockets including pockets representative of meals and snacks of a planned daily diet
    said pockets of each said arrangement being aligned in its respective panel according to the sequence in time in which the respective meals and snacks of said diet are to be consumed,
    a series of cards corresponding to and identifying food group choices of said diet,
    said food group cards being assembled into sets matched to said respective meals and snacks of said diet
    said card sets being placed in corresponding meal and snack pockets of one of said panels,
    said cards each being arranged for withdrawal from its respective pocket of said one panel and transfer to the corresponding pocket of the other of said panels when the diet food which it represents is consumed whereby a current indication is provided on said one panel as to which of the diet foods were consumed while at the same time also preparing the diet program for the following day represented on said panel.

4. A diet plan aid according to claim 3 in which each food group card includes a list of several optional food items of the respective food group which it represents and the portion of each such item allowed in the diet.

5. A diet plan aid according to claim 3 in which each food group card is provided a pictorial symbol representative of the diet group.

6. A diet plan aid according to claim 4 in which cards representative of the same food group include cards each having a different listing of optional food items of the diet whereby cards can be assembled in sets for each of the meals and snacks including all items of the diet.

7. A diet plan aid according to claim 3 in which said cards include a card representative and identified for medicine to be taken at specific times as the diet plan is followed.

8. A diet plan aid according to claim 3 in which said cards include a card representative and identified for exercise to be conducted at specific times for which pockets are provided on said panels as the diet is followed.

9. A diet plan aid according to claim 3 in which marking space associated with each pocket is provided for the user to optionally mark the prescribed time when items of cards in said pocket are to be consumed.

10. A diet plan aid according to claim 3 wherein the pockets of said panels corresponding to the meals and snacks of the diet are each provided with a pictorial illustration of a clock face showing the average time of day for consumption of the respective meals and snacks.

11. A diet plan method wherein cards listing items of a planned diet are assembled into sets of cards each representative of foods to be consumed at designated times placing each of said sets of cards into a pocket representative of a designated food consumption time during which the specified items of the sets are to be consumed withdrawing each card representative of an item of food of the diet from its respective pocket when such item is consumed and placing the withdrawn card into a pocket corresponding to a designated time for consumption of such item of food on a subsequent day of the diet whereby a visual indication is provided of items consumed as the diet is followed and also preparing the cards in sets in pockets for consumption at planned times on the subsequent day of the diet.

12. A diet plan method according to claim 11 wherein each of said cards includes a list of specific items and portions thereof allowed according to said diet and from which listing sub-groups of cards are assembled to match the meals and snacks of said planned diet and are placed in the corresponding meal and snack pockets of a given panel, withdrawing from its respective pocket a card corresponding to the specified item of food of the diet when said specified item of food is consumed, and placing said card in the corresponding meal or snack pocket of another identical panel.

13. A diet plan method according to claim 12 wherein the cards are progressively withdrawn from each of said pockets and placed in the corresponding pockets of the other of said panels and said withdrawal of cards is effected repetitively through a full day of the diet whereby all food cards are transferred to the pockets of the said other panel thereby providing the program for the planned diet for a subsequent day.

14. A method for teaching and learning a planned diet utilizing a folder and cards representative of food items; said folder comprising two panels; said panels each having pockets identified for breakfast, lunch, dinner and snack times for a given day; said cards having listings of food items of the diet allowed for consumption;
said method comprising assembling cards in sets listing items for each of the diet meals and snacks;
matching said card sets each with its respective meal and snack pocket of one of said panels and placing it in said pocket;
as each item listed on a card is consumed removing it from its respective pocket and placing it into the corresponding pocket of the other of the panels; and
repeating the procedure for each meal and snack consumed during the given day whereby at the end of the given day the cards will be transferred to the pockets of the other panel in programmed order for the next day of the diet.

* * * * *